US006929474B2

(12) United States Patent
Schenck et al.

(10) Patent No.: US 6,929,474 B2
(45) Date of Patent: Aug. 16, 2005

(54) SUPPORT APPARATUS FOR SUPPORTING COMPONENTS OF DENTAL MATERIAL

(75) Inventors: Laurent Schenck, Frastanz (AT); Philipp Gabriel, Leipzig (GB); Steffen Riethmuller, Stuttgart (DE)

(73) Assignee: Ivoclar Vivadeat, AG, Schaan (LI)

( * ) Notice: Subject to any disclaimer, the term of this patent is extended or adjusted under 35 U.S.C. 154(b) by 265 days.

(21) Appl. No.: 10/290,075

(22) Filed: Nov. 7, 2002

(65) Prior Publication Data

US 2004/0058296 A1 Mar. 25, 2004

(30) Foreign Application Priority Data

Sep. 24, 2002 (DE) ......................................... 102 44 424

(51) Int. Cl.[7] ................................................. A61C 1/14
(52) U.S. Cl. ........................ 433/49; 215/230; 215/295; 206/223; 206/219
(58) Field of Search ...................... 433/49, 77; 422/61; 206/219, 220, 221, 534, 223, 570, 229, 575, 63.5, 514, 501, 563, 1.8; 215/10, 365, 230, 395

(56) References Cited

U.S. PATENT DOCUMENTS

| | | | |
|---|---|---|---|
| 2,890,816 A | * | 6/1959 | Horland .................... 222/142.3 |
| 3,278,007 A | * | 10/1966 | Weber ......................... 206/1.8 |
| 3,743,088 A | * | 7/1973 | Henkin ........................ 206/569 |
| 4,195,059 A | * | 3/1980 | Whitcher et al. ............. 422/61 |
| 4,785,953 A | * | 11/1988 | Buchholz et al. ........... 215/365 |
| 5,024,705 A | * | 6/1991 | Cahill .......................... 134/38 |
| 5,106,297 A | | 4/1992 | Discko |
| 5,240,415 A | | 8/1993 | Haynie |
| 5,377,823 A | * | 1/1995 | Steen et al. ................. 206/63.5 |
| 5,941,394 A | * | 8/1999 | Siegler ....................... 206/571 |
| 5,954,213 A | * | 9/1999 | Gerhart et al. ................ 215/10 |

FOREIGN PATENT DOCUMENTS

| | | |
|---|---|---|
| DE | 199 51 504 A | 5/2001 |
| DE | 201 04 819 U | 6/2001 |
| JP | 2000-85860 | 3/2000 |

* cited by examiner

Primary Examiner—Todd E. Manahan
(74) Attorney, Agent, or Firm—John C. Thompson; Alan S. Korman

(57) ABSTRACT

A support apparatus for supporting components of a dental material includes two individual bottles each capable of receiving therein a component which can be shaken. Each individual bottle has a coding associated therewith and a cover has cover regions with respective codings corresponding to the bottle coding. A mixing base has a pair of recesses each with individual coding corresponding to the coding of a respective one of the individual bottles, whereby each respective bottle has a respective cover region and a respective recess of the mixing base associated therewith and identifiable as associated therewith by virtue of the corresponding coding thereon. The individual bottles collectively comprise a bottle unit and are closeable by a common cover.

16 Claims, 4 Drawing Sheets

SUPPORT APPARATUS FOR SUPPORTING COMPONENTS OF DENTAL MATERIAL

BACKGROUND OF THE INVENTION

The present invention relates to a support apparatus for supporting components of dental material.

Numerous configurations of support apparatus for supporting components of dental material are known. Thus, for example, it is known from U.S. Pat. No. 5,240,415 to provide a support apparatus for components of a dental material. With this arrangement, a bottle deployed together with a spatula as the application element and a dental material are collectively disposed in a common packaging disposition in the manner of a blister package. Such an arrangement is, indeed, substantially hygienic and readily accessible but is not, however, suitable if, instead of a liquid and a powder-type component, two liquids are to be used.

It is additionally known, from U.S. Pat. No. 5,106,297, to provide a support apparatus by which a mixing base can be configured in various forms for differing dental components. In this arrangement, the bottles having corresponding liquids such as bond material or other liquids can be disposed in two identical depressions or recesses. Also here, as well, there follows a certain shape identity code—that is, an identification based on corresponding geometries each associated with a respective item intended to indicate an association between the items —in the form of shoulders on the recesses intended to correspond to the bottles which are to be distinguished from one another.

In fact, in the various configurations of the recesses, a certain orientation is made available for the dentist or the dental technician. Also here, however, there exists the danger that the liquids, which should not be put together with one another, may be inadvertently disposed in the wrong recess. The mixing base is, in this instance, unusable, as it cannot be ensured that the remnants of the other liquid are not in the respective recesses.

JP-2000/85860 discloses a multi-faceted arrangement of bottles which can receive the dental materials. Each bottle includes a cap and the caps of the two bottles are differently configured relative to one another in order to make possible a more facile differentiation between the two bottles.

Both bottles are received in a common bottle holder. They are seated in the bottle holder in a disposition sufficiently secure that an application of the respective liquids should be possible without one of the individual bottles falling out of the bottle holder. Special imprint surfaces are provided to offer the possibility of an imprint, by which the respective bottle corresponding to the bottle holder can be identified. Additionally, a cover is provided which commonly covers both bottles.

In this conventional arrangement, it is possible to remove one bottle or, as well, both empty bottles, from the bottle holder and replace the respective bottle(s) with a new bottle or new bottles. In this connection, there exists, to be sure, the danger that the positions of two bottles will be mixed-up, as the two receipt configurations for the bottles exhibit substantially the same dimensions. Continuously present remainders of the dental components, which have linked with the right or the left regions of the cover or, respectively, the bottle holder, can come into contact with the other bottle or with the components stored therein, which can lead to corresponding reactions. It is also not ensured that there is not a mix-up in connection with a mixing operation on the mixing base of the respective liquids.

In connection with the concepts "mixing" and "mixing base", these concepts are to be understood as referring to the preparation work on a mixing base, by which, as desired (but not obligatorily), a further component can be added to the respective component. The respective components on the mixing base are removed from the respective recess by an application element and applied to the tooth of the patient. In this connection, it is especially important, in connection with, for example, a primer with which a tooth surface is etched in preparation for a restoration thereof, that the primer does not come into contact with a bonding material, whereby such avoidance of contact of the primer and the bonding material makes available the correspondingly expected quality of the restoration result and prevents the continuous occurrence of demands for redress action. Conversely, the bonding material should be kept from contact with the primer to the extent possible, as this will otherwise significantly impair the quality of the restoration result.

On the other hand, it is also important, that the bottles in which the various components are received, are constantly stored in a well closed manner. With the arrangement disclosed in the above-noted Japanese patent publication, the danger exists that the dentist will forget a cap and close the cover such that it cannot be recognized that the respective bottle underneath the cover with the missing cap has not been closed. In the event that such a falsely stored component is, nonetheless, deployed, the quality of the restoration result is, in any event, impaired.

SUMMARY OF THE INVENTION

The present invention provides a solution to the challenge of providing a support devise which offers an improved security arrangement while the same quality of the restoration result is preserved.

The inventive solution is exemplified through the realization of a support apparatus having a plurality of bottles which are connected to one another in a shape interlocking manner, are closeable with a cover, and which collectively form a bottle unit. In this manner, it is ensured that a separate bottle holder is not required which would otherwise disadvantageously create the possibility of a mix-up of the bottles. At the same time, the inventive solution is a cost-favorable solution as there is no longer the need to configure the bottle holder from separately produced components.

Particular advantages are offered through the inventive closure of the individual bottles with a common cover. On the one hand, this ensures that no inwardly disposed cap can be forgotten, as the cover itself seals in a secure manner the outlet openings of the individual bottles. It can be confirmed that the desired sealing function has been ensured by the provision of a corresponding snap position. Via the inventive coding on each individual bottle, which coincides with the associated coding of the cover and the mixing base, a maximum security protecting against mix-ups and false exchanges is ensured. Preferably, the coding of the cover is a shape identity coding so that it is ensured that the cover cannot be falsely disposed on another bottle arrangement.

Preferably, a double coding is provided in order to increase still further the security against mix-ups. In this manner, the respective interrelated association can, for example, be made clear through a corresponding graphic and/or color emblem on the individual bottle and the mixing base. Additionally, the serial usage order of the bottles can be signaled by a number or a letter and, also, the interrelated association can be reinforced by use of numbers or letters respectively corresponding to one another.

The inventive solution additionally offers the advantage that the corresponding measures ensuring against mix-ups can be expanded as well in the domain of the application of the dental components by correspondingly denominated application elements such as a brush or, as desired, a spatula.

In accordance with the present invention, it is especially advantageous that, in spite of the use of a cover produced by a cost-favorable production process and which ensures the sealing function, a seal-tight sealing function is possible so that, as well, in connection with oscillations in the air pressure in the storage region, the introduction of contaminating air is foreclosed. In this connection, the cover includes posts preferably configured as tube closure posts which are inserted into the outlet openings and provide sealing thereat. A preferred configuration of a closure system of this type is described hereinafter.

In accordance with the present invention, it is particularly advantageous that the number or plurality of individual components needed for the availability of a handling system is clearly reduced. Instead of six individual components, only three individual components need be produced and maintained.

BRIEF DESCRIPTION OF THE DRAWINGS

Further advantages, details, and features are set forth in the hereinafter following description of the embodiment of the invention as described in connection with the drawings, in which.

DETAILED DESCRIPTION OF THE PREFERRED EMBODIMENT

Figure 1:
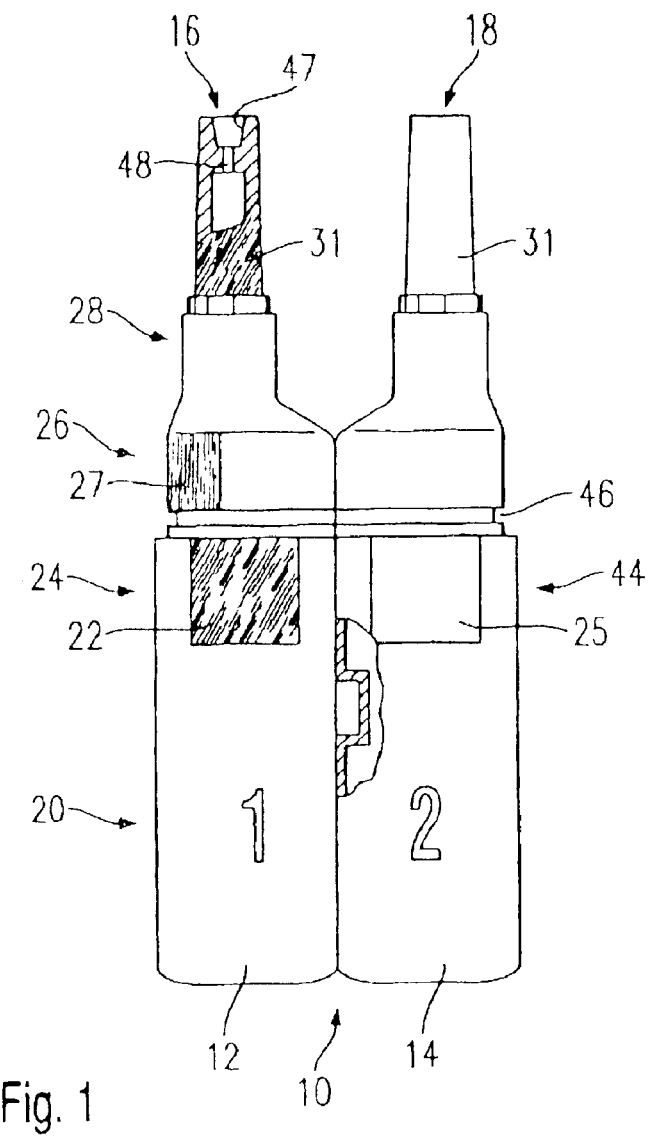
FIG. 1 is a schematic side elevational view of one embodiment of the support apparatus of the present invention, whereby a bottle unit is illustrated.

As seen in FIG. 1, the bottle unit 10 shown therein comprises two individual bottles 12 and 14 which are connected to one another in a special manner. Each individual bottle includes a component capable of being shaken, the component being, especially, a liquid, and each bottle 12, 14 is provided with an outlet opening 16, 18, respectively, through which the withdrawal of the liquid from the bottle is possible. In the illustrated embodiment, each individual bottle is provided with three codings. First, a symbol coding 20 is provided—in the illustrated embodiment, the symbol coding is characterized by the provision of the numbers "1" and "2" on the front sides of the individual bottles 12 and 14, respectively.

Additionally, a color coding 22 is provided on each individual bottle. In this connection, the individual bottle 12 includes a black color field 24 and the individual bottle 14 includes a green color field 25. Also, as well, the two color fields are provided at generally the same height.

As can be further seen in FIG. 1, the outlet openings in the necks of the individual bottles 12 and 14 are configured in corresponding cannula 29 and 31, respectively. The cannula 29 is configured in the color black corresponding to the black color field 24 on the individual bottle 12. Conversely, the cannula 31 is configured in green corresponding to the green color field 25 of the individual bottle 14 on which the cannula 31 is disposed.

Each individual bottle additionally comprises a shape identity coding 26. In this connection, the individual bottle 12 includes an inclined surface 27 adjacent its neck 28 while the individual bottle 14 is characterized by the absence of a corresponding inclined surface.

Figure 5:
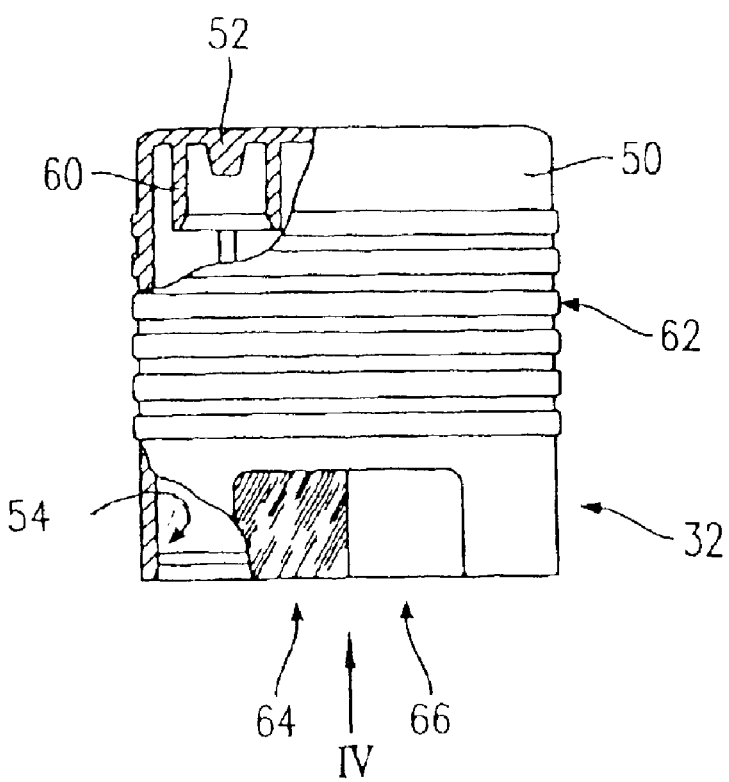
FIG. 5 is a side elevational view of the cover shown in FIG. 4.
Figure 6:
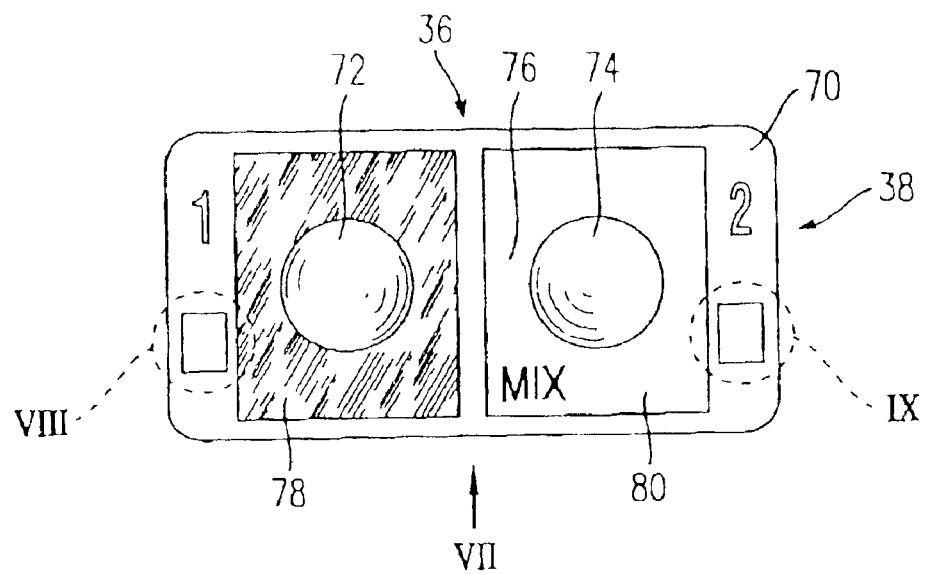
FIG. 6 is a top plan view of a further component of the inventive support apparatus—namely, a mixing base.

It is provided that an interrelated association is established by at least two codings on the cover as well as the mixing base and that an interrelated association is established by at least one coding on each respective application element. In the illustrated embodiment, the cover is provided with a color coding 32 and a shape identity coding 34 and the mixing base is provided with a color coding 36 and a symbol coding 38, as can be seen in FIGS. 5 and 6.

The necks 28 of both individual bottles 12 and 14 extend upwardly from the bodies of the respective bottles. The necks are disposed substantially outwardly in order to provide a comparatively large distance between the outlet openings 16 and 18.

Both individual bottles 12 and 14 are connected to one another via projections 40 and recesses 42. This can be seen by a comparison of FIGS. 1 and 2 with one another. The dimensions of the projections 40 and the recesses 42 are selected such that both individual bottles 12 and 14 remain secured to one another as well when the dentist grips only one bottle.

However, both individual bottles 12 and 14 can, in addition, be separated from one another, via a significant force application thereunto, so that in principle an individual re-filling of the material from the two differing components is also possible.

Figure 2:
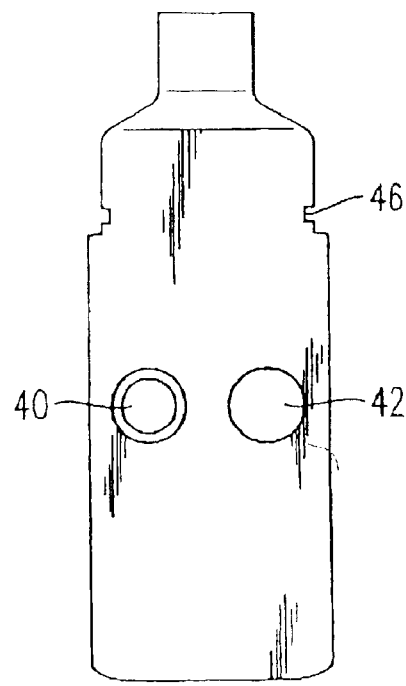
FIG. 2 is a side elevation of the respective surface of an individual bottle against which the other bottle is disposed in neighboring relation.
Figure 3:
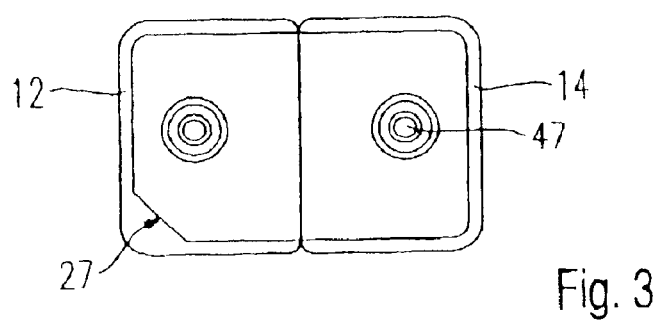
FIG. 3 is a top plan view of the bottle unit shown in FIG. 1.
Figure 4:
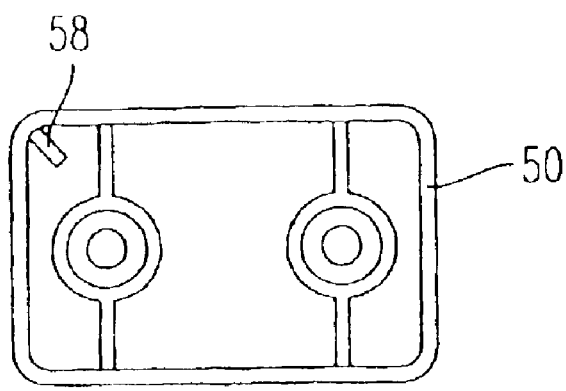
FIG. 4 is a bottom plan view of the underside of a modified cover for the inventive support apparatus which is provided for the support of the bottle unit as shown in FIG. 1.

Both individual bottles together collectively form a bottle unit 10 with a common encircling edge 44. The edge 44 includes a groove 46 which is compatibly configured with a corresponding projection on the bottom edge of the cover for the receipt of the corresponding projection therein. This can be seen in particular in FIG. 2. FIG. 2 shows the bottles without their outlet openings 16 and 18 for the purpose of simplification of the illustration. As can be seen in FIG. 1, each outlet opening 16, 18 includes a sealing surface in the form of a closure cone 47 which cooperates together with the cover 50 as shown in FIGS. 4 and 5. The cover 50 comprises, in this connection, conical posts 52 which are inserted into the closure cones 47 to securely seal the back sides of the through openings 48 which extend below the closure cones and have, as well, a comparatively small diameter. Preferably, the underside of the posts 52 are additionally provided with a sealing element formed of rubber or similar material.

The cover 50 comprises sealing surfaces for the sealing off of the outlet openings and the cover indicates, by its flush seating on the bottle unit 10, that the cover is in its closed condition.

To form a sealed closure, the cover 50 engages the respective outlet openings 16 and 18 of the individual bottles 12 and 14. The cover 50 comprises, in this connection, the sealing posts 52 which are engaged in the outlet openings 16 and 18.

The seat projection 54 of the cover 50 seats in the groove 46. In this condition, the posts 52 exert pressure on the closure cones 47 so that a secure sealing is ensured.

The individual bottles 12 and 14 each have a right-angled cross section and have straight walls in the areas thereof facing one another.

The individual bottles 12 and 14 are connected directly to one another and are connected to one another, in the area of their outlet openings 16 and 18, via the cover 50.

The inclined surface 27 seats, in the closed condition, in a blocking nose 58 of the cover 50, as seen in FIG. 4, so that a non-interchangeable inserted position of the cover 50 on the bottle unit 10 is ensured. Other suitable shape identity codings can also be deployed in this context as well.

As seen in FIG. 5, the posts 52 extend from the top side of the cover 50 downwardly. The cover is, in addition, encircled by a closure apron 60 extending around the periphery of the cover which encircles the outlet spouts of both individual bottles 12 and 14 so that, in addition, a seal in the manner of a labyrinth seal is provided. This configuration permits, as well, the assurance of a secure sealing in connection with a high pressure difference of 100 mbar or, even, 150 mbar, so that the inventive support apparatus is particularly storage stable.

The cover 50 preferably includes, on its outer side, a striation 62 which, in connection with the removal of the cover 50, facilitates overcoming the seating force of the seating projections 54 in the groove 46. As can be seen in FIG. 5, the realization of the color coding 32 and the shape identity coding 34 is possible. A region 64 of the cover is interrelatedly associated, in this connection, with the individual bottle 12 and a further cover region 66 is interrelatedly associated with the individual bottle 14. The interrelated associations are based on the two illustrated codings.

FIG. 6 shows the inventive mixing base with the color coding 36 and the symbol coding 38. The mixing base 70 includes a pair of recesses 72 and 74 whose distance between centers corresponds approximately to the distance of the outlet openings 16 and 18 so that a simultaneous and parallel removal of the respective liquids is possible.

The recesses 72 and 74 are, however, preferably provided centrally on the mixing base 70 in order to maintain at a maximum the edge spacing available to counter spillage or the like.

A bar 76 extends between the recesses 72 and 74 and has a substantial width and, at the same time, has a visually significant separation color. In the illustrated embodiment, the recess 72 is surrounded by a black color field 78 while the recess 74 is surrounded by a green color field 80.

Symbol codings are provided in the form of the numbers "1" and "2" outwardly of the color fields 78 and 80. The numbers correspond with the corresponding symbol codings 20 on the individual bottles 12 and 14 of the bottle unit 10 and offer, at the same time, an indication of the serial use pattern for the handling of the components.

Figures 8, 9:
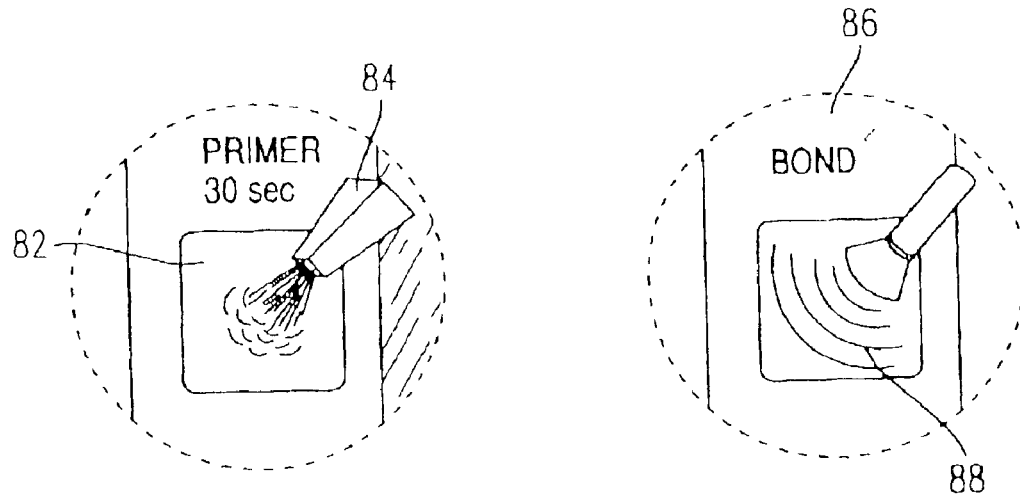
FIG. 8 is an enlarged sectional view of the mixing assembly shown in FIG. 6.
FIG. 9 is an enlarged sectional view of the mixing assembly shown in FIG. 6.

Further, usage information is provided on the mixing base 70 and, in fact, is provided on the fields VIII and IX as is shown in an enlarged manner in FIGS. 8 and 9.

Figure 7:
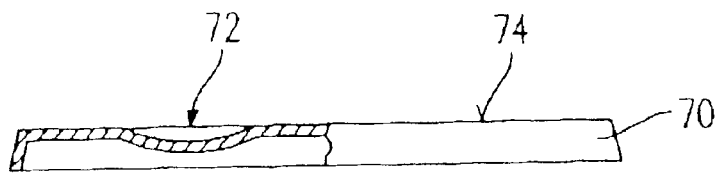
FIG. 7 is a side elevational view of the mixing base shown in FIG. 6, the mixing base being shown in partial section.

As can be seen in FIG. 7, the mixing base 70 comprises the two respective ball-shaped recesses 72 and 74 neither of which fully extends to the underside of the mixing base. The mixing base 70 can be manufactured in a substantially cost-favorable manner as a single piece which also facilitates the imprinting of the inventive codings thereon.

FIG. 8 shows a usage information component 82, which is configured as a so-called primer and which is configured to act within 30 seconds, whereby a blow drying symbol 84 is shown which indicates that a blow drying process is to be subsequently undertaken.

The usage information 86 in the area of the recess 74 shows, in contrast, an imprint of the word "bond", indicating a bonding material, as well as a stylized light hardening device 88, which make clear that a light hardening step for the restoration component is desired.

Figure 10:
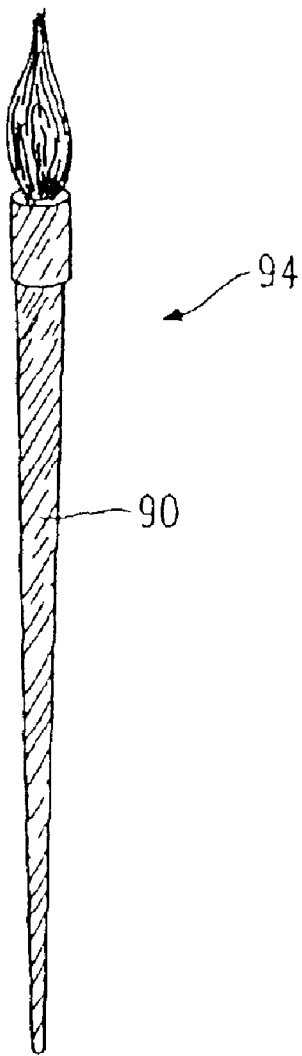
FIG. 10 is a view of a respective one of the application elements associated with the one embodiment of the support apparatus of the present invention.
Figure 11:
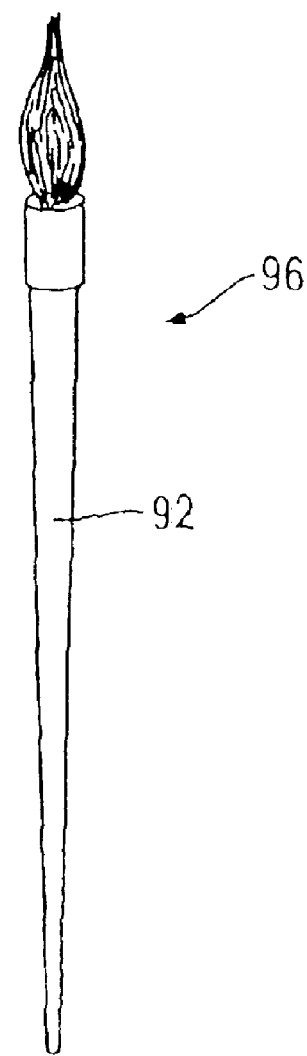
FIG. 11 is a view of a respective one of the application elements associated with the one embodiment of the support apparatus of the present invention.

FIGS. 10 and 11 each show a respective application element in the form of brushes. Also here the color codings 90 and 92 are provided which, in the two locations, signal or indicate the desired colors black and green. It is to be understood, that instead of this color configuration, other desired color configurations and, as well, other desired support elements, can be provided instead of the support elements 94 and 96 provided herewith.

The present invention is, of course, in no way restricted to the specific disclosure of the specification and drawings, but also encompasses any modifications within the scope of the appended claims.

What is claimed is:

1. A support apparatus for supporting components of a dental material, comprising:
   at least two individual bottles (12, 14) each capable of receiving therein a component which can be shaken, each individual bottle (12, 14) having a coding (22) associated therewith, wherein the individual bottles (12, 14) are secured to one another in a compatibly configured manner via projections 40 and recesses 42 disposed on the surfaces of the bottles facing one another;
   a cover having cover regions (64, 66), each cover region (64, 66) having a coding corresponding to the coding (22) of a respective one of the individual bottles (12 and 14); and
   a mixing base (70) having a pair of recesses (72, 74), each recess (72, 74) having a coding (78, 80) corresponding to the coding (22) of a respective one of the individual bottles (12, 14), whereby each respective bottle (12, 14) has a respective cover region (64, 66) and a respective recess (72, 74) of the mixing base (70) associated therewith and identifiable as associated therewith by virtue of the corresponding coding thereon.

2. A support apparatus according to claim 1, whereby the individual bottles (12, 14) collectively comprise a bottle unit (10) and are closeable by a common cover (50).

3. A support apparatus according to claim 2, wherein the codings on the individual bottles (12, 14) form a coding of the bottle unit (10) which indicates the respective seated position of the cover (50) relative to the individual bottles (12, 14) and the bottle unit (10).

4. A support apparatus according to claim 2, wherein the bottle unit (10) includes a seat into which the cover (50) seats in the closure position.

5. A support apparatus according to claim 1, wherein the recesses (72, 74) of the mixing base (70) include locations for the receipt of tips of application elements (94, 96) provided for applying the components contained in the bottles (12, 14) and each application element (94, 96) has a coding corresponding to the respective coding of the associated individual bottle (12, 14).

6. A support apparatus according to claim 1, wherein the codings are at least one of a shape identity coding (28) and a color coding (22).

7. A support apparatus according to claim 1, wherein the individual bottles (12, 14) include respective outlet openings (16, 18), the cover (50) includes sealing posts (52), and the cover (50) is disposable on the individual bottles (12, 14), in a manner such that the sealing posts (52) sealingly close the outlet openings (16, 18).

8. A support apparatus according to claim 1, wherein the cover (50) as well as one individual bottle (12) includes a shape identity coding (58), which prevents a false disposition of the cover on the bottle unit (10).

9. A support apparatus according to claim 1, wherein both individual bottles (12, 14) are connected with one another and their outlet openings (16, 18) are closeable in a sealed manner by areas of the cover in a manner which maintains the closure of the outlet openings in resistance to pressure differentials.

10. A support apparatus according to claim 1, wherein the individual bottles (12, 14) include respective outlet openings (16, 18), wherein the distance between the outlet openings (16, 18) of the individual bottles (12, 14) corresponds to the difference between the recesses (72, 74) of the mixing base (70).

11. A support apparatus according to claim 1, wherein the pair of recesses (72, 74) of the mixing base (70) are at a spacing from one another and each has its own different color and the coding (78, 80) of the recesses (72, 74) corresponds to the coding (22) of a respective one of the individual bottles (12, 14).

12. A support apparatus according to claim 11, wherein the double coding is comprised of a selected one of a color coding (22) and a shape identity coding (28) and a color coding (22) and a symbol coding (20).

13. A support apparatus according to claim 1, and further comprising a bar (76) separating the recesses (72, 74), the bar (76) being configured, of a differentiating color.

14. A support apparatus according to claim 1, wherein the pair of recesses (72, 74) of the mixing base (70) are arranged substantially centrally of the mixing base (70) and the mixing base (70) includes, along its edges, indicia fields (86) which support thereon usage information.

15. A support apparatus according to claim 1, wherein the individual bottle (12, 14) include respective outlet openings (16, 18) wherein the outlet openings (16, 18) comprise respective cannula (29, 31), which are compatibly configured with the individual bottles (12, 14) for interconnection therewith.

16. A support apparatus according to claim 15, wherein the cannula (29, 31) each comprise a coding which corresponds to the coding (22) of the associated individual bottle (12, 14).

* * * * *

UNITED STATES PATENT AND TRADEMARK OFFICE
CERTIFICATE OF CORRECTION

PATENT NO. : 6,929,474 B2  Page 1 of 1
APPLICATION NO. : 10/290075
DATED : August 16, 2005
INVENTOR(S) : Laurent Schenck et al.

It is certified that error appears in the above-identified patent and that said Letters Patent is hereby corrected as shown below:

Column 15
Claim 15, line 2, "bottle" should be --bottles--;
Claim 15, line 3, after "(16, 18)" first occurrence, a --,-- should be inserted.

Signed and Sealed this

Third Day of July, 2007

JON W. DUDAS
*Director of the United States Patent and Trademark Office*